(12) United States Patent
Seifert et al.

(10) Patent No.: US 10,349,978 B2
(45) Date of Patent: Jul. 16, 2019

(54) OPEN CHANNEL IMPLANT TOOL WITH ADDITIONAL LUMEN AND IMPLANT TECHNIQUES UTILIZING SUCH TOOLS

(71) Applicant: Medtronic, Inc., Minneapolis, MN (US)

(72) Inventors: Kevin R. Seifert, Forest Lake, MN (US); Nathan L. Olson, Shoreview, MN (US); Becky L. Dolan, Chisago, MN (US)

(73) Assignee: Medtronic, Inc., Minneapolis, MN (US)

(*) Notice: Subject to any disclaimer, the term of this patent is extended or adjusted under 35 U.S.C. 154(b) by 99 days.

(21) Appl. No.: 14/973,800

(22) Filed: Dec. 18, 2015

(65) Prior Publication Data
US 2016/0175008 A1    Jun. 23, 2016

Related U.S. Application Data

(60) Provisional application No. 62/093,507, filed on Dec. 18, 2014.

(51) Int. Cl.
A61B 17/34 (2006.01)
A61N 1/05 (2006.01)
(Continued)

(52) U.S. Cl.
CPC .. *A61B 17/3468* (2013.01); *A61B 17/320016* (2013.01); *A61N 1/05* (2013.01);
(Continued)

(58) Field of Classification Search
CPC .... A61B 2017/320056; A61B 17/3468; A61B 10/0275; A61B 17/320016;
(Continued)

(56) References Cited

U.S. PATENT DOCUMENTS 4,030,509 A   6/1977   Heilman et al.
4,146,037 A   3/1979   Flynn et al.
(Continued)

FOREIGN PATENT DOCUMENTS

CN   2364868 Y    2/2000
CN   101502699 A  8/2009
(Continued)

OTHER PUBLICATIONS

Obadia, et al., "New Approach for Implantation of Automatic Defibrillators Using Videothoracoscopy", Journal Ann Cardiol Angeiol (Paris); Sep. 1994; 43 (7) Abstract Only, 1 page.
(Continued)

*Primary Examiner* — Eric J Rosen
*Assistant Examiner* — Brooke Labranche

(57) ABSTRACT

This disclosure provides various embodiments of implant tools and implant techniques utilizing those tools. In one embodiment, an implant tool comprises a handle and a shaft. The shaft includes a proximal end adjacent the handle, a distal end, an open channel that extends from near the proximal end to the distal end, and at least one lumen that extends from a proximal end of the shaft to a location near the distal end of the shaft. The implant tool may also include a coupler configured to connect to a fluid delivery device. In one example, the fluid delivery device may be a syringe. In some instances, the handle of the implant tool may include a compartment or a recess configured to receive the fluid delivery device.

12 Claims, 13 Drawing Sheets

(51) Int. Cl.
*A61B 17/32* (2006.01)
*A61B 17/00* (2006.01)

(52) U.S. Cl.
CPC .. *A61N 1/0504* (2013.01); *A61B 2017/00026* (2013.01); *A61B 2017/00424* (2013.01); *A61B 2017/320056* (2013.01)

(58) Field of Classification Search
CPC ........... A61B 2017/00026; A61B 2017/00424; A61B 17/8819; A61N 1/0504; A61N 1/05; A61M 5/3291; A61M 2025/004; A61M 2025/0175; A61M 2025/0681; A61M 25/0026; A61M 25/0032; A61M 2005/3201; A61M 5/3298
See application file for complete search history.

(56) References Cited

U.S. PATENT DOCUMENTS

| | | |
|---|---|---|
| 4,207,903 A | 6/1980 | O'neill |
| 4,270,549 A | 6/1981 | Heilman |
| 4,280,510 A | 7/1981 | O'Neill |
| 4,291,707 A | 9/1981 | Heilman et al. |
| 4,424,818 A | 1/1984 | Doring et al. |
| 4,437,475 A | 3/1984 | White |
| 4,512,351 A | 4/1985 | Pohndorf |
| 4,538,624 A | 9/1985 | Tarjan |
| 4,644,957 A | 2/1987 | Ricciardelli et al. |
| 4,765,341 A | 8/1988 | Mower et al. |
| 4,832,687 A | 5/1989 | Smith, III |
| 4,921,479 A | 5/1990 | Grayzel |
| 5,009,643 A | 4/1991 | Reich et al. |
| 5,036,854 A | 8/1991 | Schollmeyer et al. |
| 5,125,904 A | 6/1992 | Lee |
| 5,147,376 A | 9/1992 | Pianetti |
| 5,176,135 A | 1/1993 | Fain et al. |
| 5,255,691 A | 10/1993 | Otten |
| 5,257,973 A | 11/1993 | Villasuso |
| 5,258,003 A | 11/1993 | Ciaglia et al. |
| 5,300,106 A | 4/1994 | Dahl et al. |
| 5,312,355 A | 5/1994 | Lee |
| 5,346,502 A | 9/1994 | Estabrook et al. |
| 5,364,372 A | 11/1994 | Danks et al. |
| 5,441,504 A | 8/1995 | Pohndorf et al. |
| 5,456,699 A | 10/1995 | Armstrong |
| 5,478,329 A | 12/1995 | Ternamian |
| 5,509,924 A | 4/1996 | Paspa et al. |
| 5,613,953 A | 3/1997 | Pohndorf |
| 5,667,514 A | 9/1997 | Heller |
| 5,671,736 A | 9/1997 | Pettit et al. |
| 5,690,648 A | 11/1997 | Fogarty et al. |
| 5,752,937 A | 5/1998 | Otten et al. |
| 5,755,697 A | 5/1998 | Jones et al. |
| 5,779,715 A | 7/1998 | Tu |
| 5,782,841 A | 7/1998 | Ritz et al. |
| 5,800,398 A | 9/1998 | Hahnle et al. |
| 5,853,391 A | 12/1998 | Bell |
| 5,871,528 A | 2/1999 | Camps et al. |
| 5,871,532 A | 2/1999 | Schroeppel |
| 5,944,732 A | 8/1999 | Raulerson et al. |
| 5,951,518 A | 9/1999 | Licata et al. |
| 6,032,079 A | 2/2000 | KenKnight et al. |
| 6,104,957 A | 8/2000 | Alo et al. |
| 6,122,552 A | 9/2000 | Tockman et al. |
| 6,159,198 A | 12/2000 | Gardeski et al. |
| 6,228,052 B1 | 5/2001 | Pohndorf |
| 6,278,897 B1 | 8/2001 | Rutten et al. |
| 6,283,948 B1 | 9/2001 | McKernan et al. |
| 6,324,414 B1 | 11/2001 | Gibbons et al. |
| 6,415,187 B1 | 7/2002 | Kuzma et al. |
| 6,436,068 B1 | 8/2002 | Bardy |
| 6,445,954 B1 | 9/2002 | Olive et al. |
| 6,544,247 B1 | 4/2003 | Gardeski et al. |
| 6,605,094 B1 | 8/2003 | Mann et al. |
| 6,726,617 B1 | 4/2004 | Schmidt |
| 6,730,083 B2 | 5/2004 | Freigang et al. |
| 6,733,500 B2 | 5/2004 | Kelley et al. |
| 6,749,574 B2 | 6/2004 | O'Keefe |
| 6,770,070 B1 | 8/2004 | Balbierz |
| 6,772,014 B2 | 8/2004 | Coe et al. |
| 6,836,687 B2 | 12/2004 | Kelley et al. |
| 6,866,044 B2 | 3/2005 | Bardy et al. |
| 6,868,291 B1 | 3/2005 | Bonner et al. |
| 6,887,229 B1 | 5/2005 | Kurth |
| 7,001,396 B2 | 2/2006 | Glazier et al. |
| 7,018,384 B2 | 3/2006 | Skakoon |
| 7,033,326 B1 | 4/2006 | Pianca et al. |
| 7,069,083 B2 | 6/2006 | Finch et al. |
| 7,076,296 B2 | 7/2006 | Rissmann et al. |
| 7,117,039 B2 | 10/2006 | Manning et al. |
| 7,151,965 B2 | 12/2006 | Osypka |
| 7,194,309 B2 | 3/2007 | Ostroff et al. |
| 7,195,637 B2 | 3/2007 | Mika |
| 7,218,970 B2 | 5/2007 | Ley et al. |
| 7,229,450 B1 | 6/2007 | Chitre et al. |
| 7,288,096 B2 | 10/2007 | Chin |
| 7,316,667 B2 | 1/2008 | Lindstrom et al. |
| 7,322,960 B2 | 1/2008 | Yamamoto et al. |
| 7,361,169 B2 | 4/2008 | Reilly |
| 7,369,899 B2 | 5/2008 | Malinowski et al. |
| 7,389,134 B1 | 6/2008 | Karicherla et al. |
| 7,450,997 B1 | 11/2008 | Pianca et al. |
| 7,499,758 B2 | 3/2009 | Cates et al. |
| 7,499,759 B2 | 3/2009 | Coe et al. |
| 7,539,542 B1 | 5/2009 | Malinowski |
| 7,627,375 B2 | 12/2009 | Bardy et al. |
| 7,655,014 B2 | 2/2010 | Ko et al. |
| 7,736,309 B2 | 6/2010 | Miller et al. |
| 7,736,330 B2 | 6/2010 | Bardy |
| 7,758,590 B2 | 7/2010 | Daniele et al. |
| 7,765,014 B2 | 7/2010 | Eversull et al. |
| 7,837,671 B2 | 11/2010 | Eversull et al. |
| 7,846,088 B2 | 12/2010 | Ness |
| 7,890,191 B2 | 2/2011 | Rutten et al. |
| 7,930,040 B1 | 4/2011 | Kelsch et al. |
| 7,983,765 B1 | 7/2011 | Doan et al. |
| 8,012,127 B2 | 9/2011 | Lieberman et al. |
| 8,057,486 B2 | 11/2011 | Hansen |
| 8,060,207 B2 | 11/2011 | Wallace et al. |
| 8,065,020 B2 | 11/2011 | Ley et al. |
| 8,066,702 B2 | 11/2011 | Rittman, III et al. |
| 8,090,451 B2 | 1/2012 | Tyson, Jr. |
| 8,155,755 B2 | 4/2012 | Flynn et al. |
| 8,157,813 B2 | 4/2012 | Ko et al. |
| 8,260,436 B2 | 9/2012 | Gerber et al. |
| 8,271,094 B1 | 9/2012 | Moffitt et al. |
| 8,280,527 B2 | 10/2012 | Eckerdal et al. |
| 8,340,779 B2 | 12/2012 | Harris et al. |
| 8,340,781 B2 | 12/2012 | Konishi |
| 8,355,786 B2 | 1/2013 | Malinowski |
| 8,364,277 B2 | 1/2013 | Glukhovsky |
| 8,386,052 B2 | 2/2013 | Harris et al. |
| 8,409,233 B1 | 4/2013 | Chinn et al. |
| 8,435,208 B2 | 5/2013 | Bardy |
| 8,442,620 B2 | 5/2013 | Silipo et al. |
| 8,447,396 B2 | 5/2013 | Palti et al. |
| 8,447,398 B2 | 5/2013 | Bardy et al. |
| 8,452,421 B2 | 5/2013 | Thenuwara et al. |
| 8,454,552 B2 | 6/2013 | Bardy |
| 8,478,424 B2 | 7/2013 | Tronnes |
| 8,478,426 B2 | 7/2013 | Barker |
| 8,942,820 B2 | 1/2015 | Doerr et al. |
| 9,227,053 B2 | 1/2016 | Bonde et al. |
| 2002/0120277 A1 | 8/2002 | Hauschild et al. |
| 2002/0120294 A1 | 8/2002 | Kroll |
| 2002/0143251 A1 | 10/2002 | Richardson et al. |
| 2003/0114908 A1 | 6/2003 | Flach |
| 2003/0233115 A1 | 12/2003 | Eversull et al. |
| 2004/0054388 A1* | 3/2004 | Osypka ............... A61N 1/056 607/116 |
| 2004/0059348 A1 | 3/2004 | Geske et al. |
| 2004/0064147 A1 | 4/2004 | Struble |
| 2004/0102829 A1 | 5/2004 | Bonner et al. |

(56) References Cited

U.S. PATENT DOCUMENTS

| | | |
|---|---|---|
| 2004/0176781 A1 | 9/2004 | Lindstrom et al. |
| 2004/0210293 A1 | 10/2004 | Bardy et al. |
| 2004/0236396 A1 | 11/2004 | Coe et al. |
| 2005/0049663 A1 | 3/2005 | Harris et al. |
| 2005/0119680 A1 | 6/2005 | Dykes |
| 2005/0131505 A1 | 6/2005 | Yokoyama |
| 2005/0288758 A1 | 12/2005 | Jones et al. |
| 2006/0041295 A1 | 2/2006 | Okypka |
| 2006/0116746 A1 | 6/2006 | Chin |
| 2006/0122676 A1 | 6/2006 | Ko et al. |
| 2006/0155250 A1 | 7/2006 | Endo et al. |
| 2006/0253181 A1 | 11/2006 | Schulman et al. |
| 2006/0265047 A1 | 11/2006 | Dorn |
| 2007/0066977 A1 | 3/2007 | Assell et al. |
| 2007/0083217 A1* | 4/2007 | Eversull ............ A61B 1/00073 606/114 |
| 2007/0100409 A1 | 5/2007 | Worley et al. |
| 2007/0173900 A1 | 7/2007 | Siegel et al. |
| 2007/0203553 A1 | 8/2007 | Smits |
| 2007/0208402 A1 | 9/2007 | Helland et al. |
| 2007/0249992 A1 | 10/2007 | Bardy |
| 2008/0046056 A1 | 2/2008 | O'Connor |
| 2008/0097424 A1 | 4/2008 | Wizeman et al. |
| 2008/0103572 A1 | 5/2008 | Gerber |
| 2008/0132933 A1 | 6/2008 | Gerber |
| 2008/0132970 A1 | 6/2008 | Barolat |
| 2008/0167650 A1 | 7/2008 | Joshi et al. |
| 2008/0234717 A1 | 9/2008 | Bruszewski |
| 2008/0243219 A1 | 10/2008 | Malinowski et al. |
| 2008/0269716 A1 | 10/2008 | Bonde et al. |
| 2008/0269763 A1 | 10/2008 | Bonde et al. |
| 2009/0018603 A1 | 1/2009 | Mitelberg et al. |
| 2009/0043373 A1 | 2/2009 | Arnault De La Menardiere et al. |
| 2009/0069750 A1 | 3/2009 | Schraga |
| 2009/0076521 A1 | 3/2009 | Hansen |
| 2009/0157091 A1 | 6/2009 | Buysman |
| 2009/0222021 A1 | 9/2009 | Chang |
| 2009/0259283 A1 | 10/2009 | Brandt et al. |
| 2009/0264780 A1 | 10/2009 | Schilling |
| 2010/0016935 A1 | 1/2010 | Strandberg et al. |
| 2010/0030227 A1 | 2/2010 | Kast et al. |
| 2010/0030228 A1 | 2/2010 | Havel |
| 2010/0056858 A1 | 3/2010 | Mokelke et al. |
| 2010/0094252 A1 | 4/2010 | Wengreen et al. |
| 2010/0113963 A1 | 5/2010 | Smits et al. |
| 2010/0125194 A1 | 5/2010 | Bonner et al. |
| 2010/0137879 A1 | 6/2010 | Ko et al. |
| 2010/0152747 A1 | 6/2010 | Padiy et al. |
| 2010/0198229 A1* | 8/2010 | Olomutzki ....... A61B 17/32053 606/129 |
| 2010/0217298 A1 | 8/2010 | Bardy |
| 2010/0217301 A1 | 8/2010 | Bardy |
| 2010/0249696 A1 | 9/2010 | Bardy |
| 2010/0268024 A1 | 10/2010 | Brannon |
| 2010/0305428 A1 | 12/2010 | Bonner et al. |
| 2010/0318098 A1 | 12/2010 | Lund et al. |
| 2011/0009877 A1 | 1/2011 | Thenuwara et al. |
| 2011/0009933 A1 | 1/2011 | Barker |
| 2011/0022057 A1 | 1/2011 | Eigler et al. |
| 2011/0224680 A1 | 9/2011 | Barker |
| 2011/0224681 A1 | 9/2011 | McDonald |
| 2011/0257660 A1 | 10/2011 | Jones et al. |
| 2012/0016377 A1 | 1/2012 | Geroy |
| 2012/0029335 A1 | 2/2012 | Sudam et al. |
| 2012/0078266 A1 | 3/2012 | Tyson, Jr. |
| 2012/0089153 A1 | 4/2012 | Christopherson et al. |
| 2012/0097174 A1 | 4/2012 | Spotnitz et al. |
| 2012/0191106 A1 | 7/2012 | Ko et al. |
| 2012/0209283 A1 | 8/2012 | Zhu |
| 2012/0209285 A1 | 8/2012 | Barker et al. |
| 2012/0290057 A1 | 11/2012 | Boling et al. |
| 2013/0103049 A1 | 4/2013 | Bonde |
| 2013/0110159 A1 | 5/2013 | Litvack et al. |
| 2013/0158564 A1 | 6/2013 | Harris et al. |
| 2013/0238067 A1 | 9/2013 | Baudino |
| 2013/0253260 A1* | 9/2013 | Lund ................. A61B 17/0401 600/30 |
| 2013/0296879 A1 | 11/2013 | Lazeroms et al. |
| 2013/0317583 A1 | 11/2013 | Pianca |
| 2014/0012292 A1 | 1/2014 | Stewart et al. |
| 2014/0039264 A1* | 2/2014 | Heiman ............ A61B 5/04001 600/202 |
| 2014/0073926 A1* | 3/2014 | Rajendran ............ A61M 5/142 600/458 |
| 2014/0148786 A1 | 5/2014 | Milo |
| 2014/0163655 A1 | 6/2014 | Chitre et al. |
| 2014/0276927 A1 | 9/2014 | Barker |
| 2014/0330208 A1 | 11/2014 | Christie et al. |
| 2014/0336581 A1 | 11/2014 | Collin |
| 2015/0032142 A1* | 1/2015 | Silvestro ............ A61B 17/3415 606/185 |
| 2015/0105793 A1 | 4/2015 | Cole |
| 2015/0133951 A1 | 5/2015 | Seifert et al. |
| 2015/0133952 A1 | 5/2015 | Seifert et al. |
| 2015/0133953 A1 | 5/2015 | Seifert et al. |
| 2015/0133954 A1 | 5/2015 | Seifert et al. |
| 2015/0216519 A1 | 8/2015 | Tang et al. |
| 2015/0313633 A1* | 11/2015 | Gross ................. A61B 1/00082 606/185 |
| 2016/0157890 A1 | 6/2016 | Drake et al. |
| 2016/0158530 A1 | 6/2016 | Drake et al. |

FOREIGN PATENT DOCUMENTS

| | | |
|---|---|---|
| CN | 102202726 A | 9/2011 |
| CN | 103157181 A | 6/2013 |
| EP | 0517494 A2 | 9/1992 |
| WO | 9720530 A1 | 6/1997 |
| WO | 2001023035 A1 | 4/2001 |
| WO | 2004073506 A2 | 9/2004 |
| WO | 2010045228 A2 | 4/2010 |
| WO | 2013076213 A1 | 5/2013 |

OTHER PUBLICATIONS

Lemmer, "Defibrillator Patch Constriction, Letter to the Editor", The Annals of Thoracic Surgery, 1996, 1 page.

Ely et al., "Thoracoscopic Implantation of the Implantable Cardioverter Defibrillator", Minimally Invasive Techniques; (Can be found on the World-Wide Web at http://chestioumal.chestpubs.org on May 6, 2013); dated Jan. 1993; 2 pages.

Damiano, "Implantation of Cardioverter Defibrillators in the Post-Sternotomy Patient", The Annals of Thoracic Surgery, 1992; 53: pp. 978-983.

Piccione, et al., "Erosion of Extrapericardial Implantable Cardioverter Defibrillator Patch Through the Gastic Fundus with Fistulous Tract Information", Cardiology in Review; 2006; 14, e21-e23 pages.

Vyhmeister et al., "Simple Approach for Extrapericardial Placement of Defibrillator Patches via Median Sternotomy", The Annals of Thoracic Surgery; 1994; 57: 4 pages.

Harman et al., "Differences in the Pathological Changes in Dogs' Hearts After Defibrillation with Extrapericardial Paddles and Implanted Defibrillator Electrodes", Journal of Pacing and Clinical Electrophysiology, Feb. 1991; vol. 14; Part 2; 5 pages.

Obadia et al., "Thoracoscopic Approach to Implantable Cardioverter Defibrillator Patch Electrode Implantation", Pacing and Clinical Electrophysiology; Jun. 1996; vol. 19; 6 pages.

Shapira, et al., A Simplied Method for Implantation of Automatic Cardioverter Defibrillator in Patients with Previous Cardiac Surgery, Pacing and Clinical Electrophysiology, January Part I, 1993, vol. 16; 6 pages.

Quigley et al., "Migration of an Automatic Implantable Cardioverter-Defibrillator Patch Causing Massive Hemothorax", Journal Texas Heart Institute, Nov. 1, 1996; vol. 23, 4 pages.

Karwande et al., Bilateral Anterior Thoracotomy for Automatic Implantable Cardioverter Defibrillator Placement in Patients with Previous Sternotomy, The Annals of Thoracic Surgery; Oct. 1992; 54(4); 3 pages.

(56) References Cited

OTHER PUBLICATIONS

Bielefeld et al., "Thoracoscopic Placement of Implantable Cardioverter-Defibrillator Patch Leads in Sheep", Circulation; Nov. 1993, vol. 88, No. 5, Part 2; 5 pages.
Frame et al., "Long-Term Stability of Defibrillation Thresholds with Intrapericardial Defibrillator Patches", Pacing and Clinical Electrophysiology, Jan. 1993, Part II, vol. 16, 6 pages.
Lawrie et al., "Right Mini-Thoracotomy: An Adjunct to Left Subcostal Automatic Implantable Cardioverter Defibrillator Implantation", The Annals of Thoracic Surgery; 1989; 47; 4 pages.
Mitchell et al., "Experience with an Implantable Tiered Therapy Device Incorporating Antitachycardia Pacing and Cardioverter/Defibrillator Therapy", Thoracic and Cardiovascular Surgery, Abstract Only, Mar. 1993, 1 page.
Bolling et al., "Automatic Internal Cardioverter Defibrillator: A Bridge to Heart Transplantation", Heart Lung Transplantation, Abstract Only, Jul.-Aug. 1991, 1 page.
Steinke et al., Subepicardial Infarction, Myocardial Impression, and Ventricular Penetration by Sutureless Electrode and Leads, Chest; 70: Jul. 1, 1976, 2 pages.
Avogadros Lab Supply Inc., Catalog; Scoopula with Beech Wood Handle, can be found on-line at http://www.avogadro-lab-supply.com/search.php, accessed Oct. 6, 2013, 1 page.
Medtronic, Inc. 6996SQ Subcutaneous, Unipolar Lead with Defibrillation Coil Electrode, Technicial Manual, 22 pages.
Medtronic, Inc. 6996T Tunneling Tool, Technical Manual, 12 pages.
Pebax Product Brochure, 14 pages and can be found on-line at http://www.pebax.com/export/sites/pebax/.content/medias/downloads/literature/pebax-product-range-brochure.pdf, 14 pages.
Cigna et al., A New Technique for Substemal Colon Transposition with a Breast Dissector: Report of 39 Cases, Journal of Plastic, Reconstructive and Aesthetic Surgery, 2006:59, 4 pages.
Tung et al., "Minimal Invasive Extra Cardiac Placement of High Voltage Defibrillator Leads", Poster 3; S200 Abstract, PO-3-4; St. Paul Hospital, Vancouver, British Columbia, Canada, 1 page.
Molina et al, "An Epicardial Subxiphoid Implantable Defibrillator Lead: Superior Effectiveness After Failure of Stndard Implants", From the Department of Surgery, Division of Cardiovascular and Thoracic Surgery and the Department of Medicine, Cardiac Arrhymthmia Center, University of Minnesota Medical School, Minneapolis, Minnesota, Pace, vol. 27, Nov. 2004, 7 pages.
Boston Scientific, Emblem S-ICD Subcutaneous Electrode Insertion Tool, Model 4711 User Manual, Feb. 1, 2015, accessed from https://web.archive.org/web/20151025171513/https://www.bostonscientific.com/manuals/manuals/landing-page/US-english.html, 28 pp.
Greatbatch Medical, OptiSeal Valved Peelable Introducer Brochure, 2010, 2 pp. (Applicant points out, in accordance with MPEP 609.04(a), that the year of publication, 2010, is sufficiently earlier than the effective U.S. filing date Dec. 18, 2014, so that the particular month of publication is not in issue.).
Prosecution History from U.S. Appl. No. 14/962,485, dated Jul. 13, 2017 through May 24, 2018, 52 pp.
Prosecution History from U.S. Appl. No. 14/962,541, dated Feb. 7, 2018 through May 7, 2018, 17 pp.
Prosecution History from U.S. Appl. No. 14/193,573, dated May 2, 2014 through Jul. 3, 2018, 185 pp.
Prosecution History from U.S. Appl. No. 14193,634, dated May 2, 2014 through Jan. 31, 2019, 277 pp.
Prosecution History from U.S. Appl. No. 14/196,443, dated Nov. 12, 2015 through Dec. 9, 2016, 84 pp.
Prosecution History from U.S. Appl. No. 14/196,298, dated Jul. 16, 2015 through Jan. 8, 2019, 219 pp.
Prosecution History from U.S. Appl. No. 14/962,485, dated Jun. 25, 2018 through Feb. 14, 2019, 66 pp.
Prosecution History from U.S. Appl. No. 14/962,541, dated Aug. 6, 2018 through Nov. 6, 2018, 41 pp.

\* cited by examiner

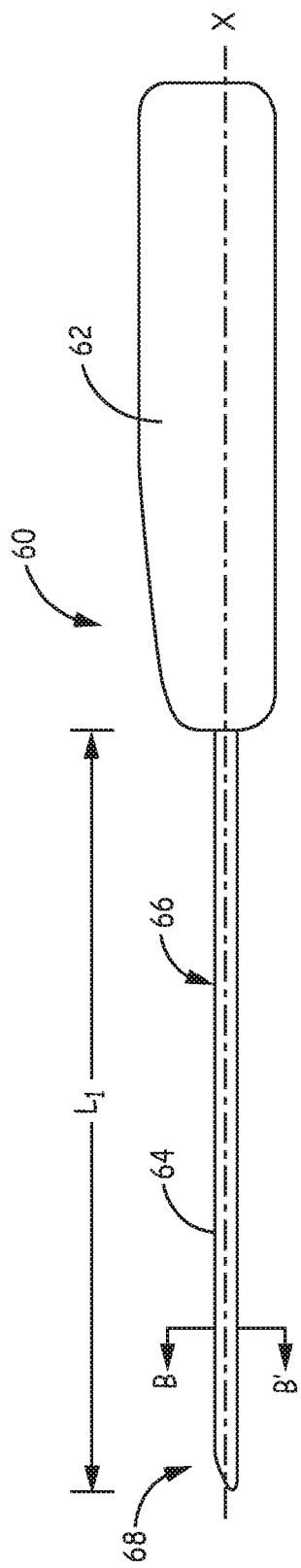
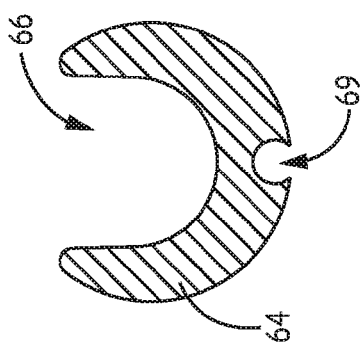
FIG. 4A
FIG. 4B
SECTION B-B'

SECTION C-C'

OPEN CHANNEL IMPLANT TOOL WITH ADDITIONAL LUMEN AND IMPLANT TECHNIQUES UTILIZING SUCH TOOLS

TECHNICAL FIELD

The present disclosure relates to implant tools and techniques for implanting implantable medical leads or other implantable components in extravascular locations.

BACKGROUND

Implantable cardiac defibrillator (ICD) systems are used to deliver high energy electrical pulses or shocks to a patient's heart to terminate life threatening arrhythmias, such as ventricular fibrillation. Traditional ICD systems include a housing that encloses a pulse generator and other electronics of the ICD and is implanted subcutaneously in the chest of the patient. The ICD is connected to one or more implantable medical electrical leads that are implanted within the heart, referred to herein as transvenous leads.

Traditional ICD systems that utilize transvenous leads may not be the preferable ICD system for all patients. For example, some patients with difficult vascular access precludes placement of transvenous leads. As another example, children and other younger patients may also be candidates for non-transvenous ICD systems. Moreover, transvenous leads may become fibrosed in the heart over time, making lead revision and extraction procedures challenging.

An extravascular ICD system may be preferred for these patients. An extravascular ICD system includes a lead (or leads) that are implanted extravascularly in the patient, e.g., outside and/or exclusive of the heart. As such, the extravascular ICD may eliminate the need to implant transvenous leads within the heart. Instead, the lead(s) may be implanted subcutaneously, substernally, or in other extravascular locations.

SUMMARY

This disclosure provides various embodiments of implant tools and implant techniques utilizing those tools. In one embodiment, an implant tool comprises a handle and a shaft. The shaft includes a proximal end adjacent the handle, a distal end, an open channel that extends from near the proximal end to the distal end, and at least one lumen that extends from a proximal end of the shaft to a location near the distal end of the shaft. The implant tool may also include a coupler configured to connect to a fluid delivery device. In one example, the fluid delivery device may be a syringe. In some instances, the handle of the implant tool may include a compartment or a recess configured to receive the fluid delivery device.

In another embodiment, an implant tool may include a handle and a shaft. The shaft includes a proximal end adjacent the handle, a distal end, a first open channel that extends from near the proximal end to the distal end, and a second open channel that extends from near the proximal end to a location near the distal end. The first open channel may have a width that is greater than or equal to an outer diameter of an implantable medical lead and the second open channel may be sized to receive a fluid delivery tube, a guide wire, a needle, a radiopaque tube/rod, an electrical probe or other structure. The implant tool may also include a fluid delivery tube within the second open channel.

In some instances, implant tool may further include a sheath configured to be placed on the shaft of the implant tool. The sheath includes a body having a proximal end and a distal end, a channel formed by the body, the channel extending from the proximal end to the distal end of the body, and an opening that extends along the body of the sheath from the proximal end to the distal end. In one example, the when the sheath is placed over the shaft of the implant tool, the first open channel of the shaft is accessible via the opening of the sheath and the body of the sheath holds the fluid delivery tube within the second open channel. In another example, when the sheath is placed over the shaft of the implant tool, a fluid delivery lumen is formed by the second open channel of the shaft and the body of the sheath. In a further example, the sheath may further include a tube integrated into the body of the sheath. The tube of the sheath may be configured to be placed within the second open channel of the shaft of the implant tool when the sheath is placed over the shaft.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF THE DRAWINGS

FIGS. 4A and 4B illustrate schematic diagrams of another example extravascular implant tool.

DETAILED DESCRIPTION

Figure 1A:
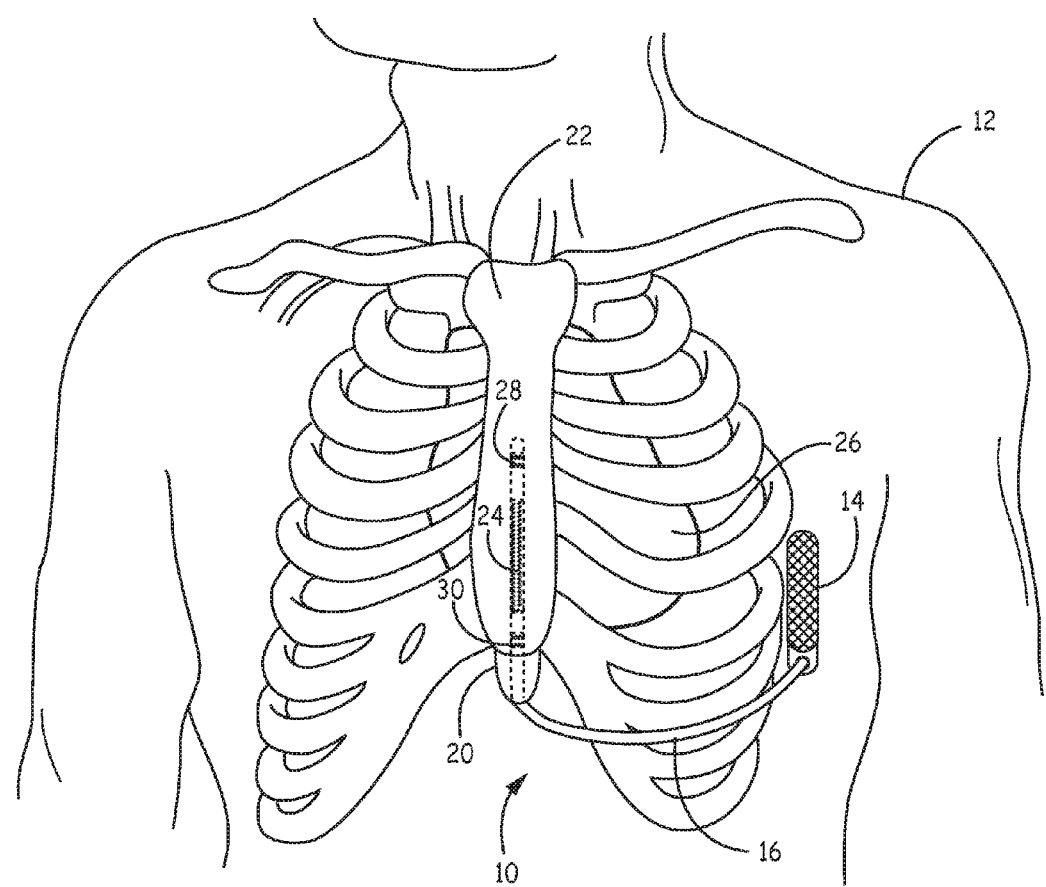
FIGS. 1A-C are conceptual diagrams of an extravascular ICD system implanted within a patient.
Figure 1B:
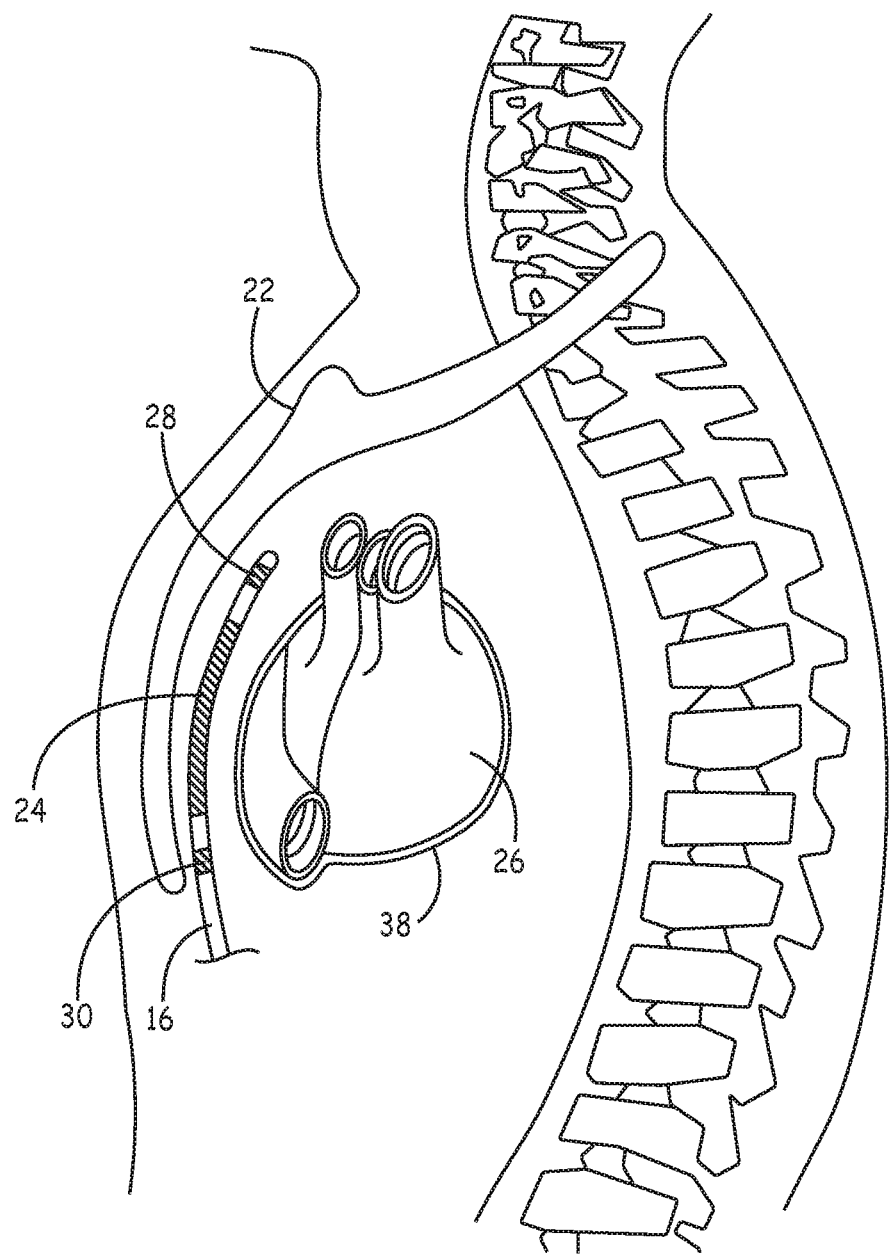
Figure 1C:
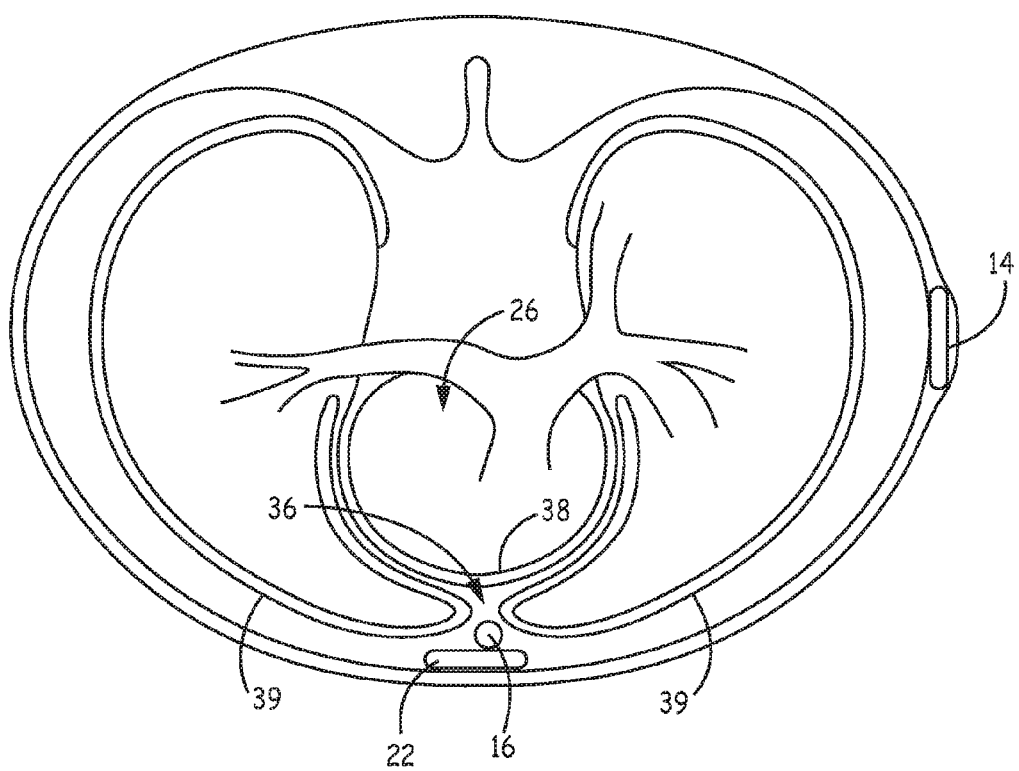

FIGS. 1A-C are conceptual diagrams of an extravascular ICD system 10 implanted within a patient 12. FIG. 1A is a front view of patient 12 implanted with ICD system 10. FIG. 1B is a side view of patient 12 implanted with ICD system 10. FIG. 1C is a transverse view of patient 12 implanted with ICD system 10. ICD system 10 includes an ICD 14 connected to a medical electrical lead 16. FIGS. 1A-C are described in the context of an ICD system capable of providing defibrillation and/or cardioversion shocks and, in some instances, pacing pulses. However, the techniques of this disclosure may also be used in the context of other implantable medical devices configured to provide other electrical stimulation therapies to the heart, or in the context of leads, devices or systems implanted to provide other therapies, such as drug pumps, neurostimulators, or other implanted medical systems.

ICD 14 may include a housing that forms a hermetic seal that protects components of ICD 14. The housing of ICD 14 may be formed of a conductive material, such as titanium, or of a combination of conductive and non-conductive materials. The conductive material of the housing functions as a housing electrode. ICD 14 may also include a connector assembly (also referred to as a connector block or header) that includes electrical feedthroughs through which electrical connections are made between lead 16 and electronic components included within the housing. The housing may house one or more processors, memories, transmitters, receivers, sensors, sensing circuitry, therapy circuitry, power sources and other appropriate components.

ICD 14 is configured to be implanted in a patient, such as patient 12. ICD 14 is on the left side of patient 12 above the ribcage. ICD 14 may, in some instances, be implanted between the left posterior axillary line and the left anterior axillary line of patient 12. ICD 14 may, however, be implanted at other subcutaneous locations on patient 12 such as at a pectoral location or abdominal location.

Lead 16 includes an elongated lead body having a proximal end that includes a connector (not shown) configured to be connected to ICD 14 and a distal portion that includes electrodes 24, 28, and 30. The implant tools and techniques of this disclosure may be used to implant lead 16 (or other type of lead or device) as described herein. Lead 16 extends subcutaneously above the ribcage from ICD 14 toward a center of the torso of patient 12, e.g., toward xiphoid process 20 of patient 12. At a location near the center of the torso, lead 16 bends or turns and extends superior under/below sternum 22 within anterior mediastinum 36. Anterior mediastinum 36 may be viewed as being bounded laterally by pleurae 39, posteriorly by pericardium 38, and anteriorly by sternum 22. In some instances, the anterior wall of anterior mediastinum 36 may also be formed by the transversus thoracis and one or more costal cartilages. Anterior mediastinum 36 includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 16 may be implanted substantially within the loose connective tissue and/or substernal musculature of anterior mediastinum 36.

In other embodiments, the distal portion of lead 16 may be implanted in other non-vascular, extra-pericardial locations, including the gap, tissue, or other anatomical features around the perimeter of and adjacent to, but not attached to, the pericardium or other portion of heart 26 and not above sternum 22 or ribcage. As such, lead 16 may be implanted anywhere within the "substernal space" defined by the undersurface between the sternum and/or ribcage and the body cavity but not including the pericardium or other portion of heart 26. The substernal space may alternatively be referred to by the terms "retrosternal space" or "mediastinum" or "infrasternal" as is known to those skilled in the art and includes the anterior mediastinum 36. The substernal space may also include the anatomical region described in Baudoin, Y. P., et al., entitled "The superior epigastric artery does not pass through Larrey's space (trigonum sternocostale)." Surg.Radiol.Anat. 25.3-4 (2003): 259-62. In other words, the distal portion of lead 16 may be implanted in the region around the outer surface of heart 26, but not attached to heart 26.

The distal portion of lead 16 may be implanted substantially within anterior mediastinum 36 such that electrodes 24, 28, and 30 are located near a ventricle of heart 26. For instance, lead 16 may be implanted within anterior mediastinum 36 such that electrode 24 is located over a cardiac silhouette of one or both ventricles as observed via an anterior-posterior (AP) fluoroscopic view of heart 26. In one example, lead 16 may be implanted such that a therapy vector from electrode 24 to a housing electrode of ICD 14 is substantially across the ventricles of heart 26. The therapy vector may be viewed as a line that extends from a point on electrode 24, e.g., center of electrode 24, to a point on the housing electrode of ICD 14, e.g., center of the housing electrode. However, lead 16 may be positioned at other locations as long as the therapy vector between electrode 24 and the housing electrode is capable of defibrillating heart 26.

In the example illustrated in FIGS. 1A-C, lead 16 is located substantially centered under sternum 22. In other instances, however, lead 16 may be implanted such that it is offset laterally from the center of sternum 22. In some instances, lead 16 may extend laterally enough such that all or a portion of lead 16 is underneath/below the ribcage in addition to or instead of sternum 22.

In the example illustrated in FIG. 1, system 10 is an ICD system that provides cardioversion/defibrillation and/or pacing therapy. However, the implant tools and techniques may be utilized to implant other types of implantable medical leads, catheters (e.g., drug delivery catheters), or other implantable component or assembly. In addition, it should be noted that system 10 may not be limited to treatment of a human patient. In alternative examples, system 10 may be implemented in non-human patients, e.g., primates, canines, equines, pigs, ovines, bovines, and felines. These other animals may undergo clinical or research therapies that may benefit from the subject matter of this disclosure.

Figure 2:
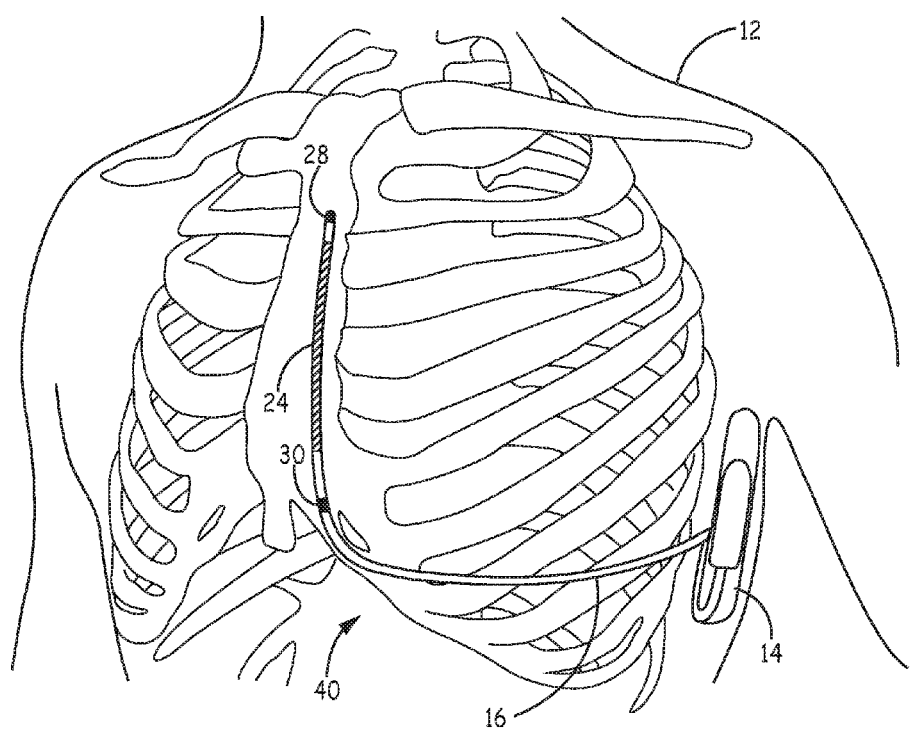
FIG. 2 is a conceptual diagram of another example extravascular ICD system 40 implanted within patient 12.

FIG. 2 is a conceptual diagram of another example extravascular ICD system 40 implanted within patient 12. In the example illustrated in FIG. 2, extravascular ICD system 40 is an implanted subcutaneous ICD system. ICD system 40 conforms substantially to ICD system 10 of FIGS. 1A-1C except that the distal portion of lead 16 is implanted subcutaneously above the sternum and/or the ribcage. In this case, ICD 14 may include additional components necessary to generate high voltage shocks at energies greater than ICD system 10, e.g., up to 80 J in the case of a subcutaneous ICD system 40 instead of 35-60 J in the case of the substernal ICD system 10.

Figure 3A:
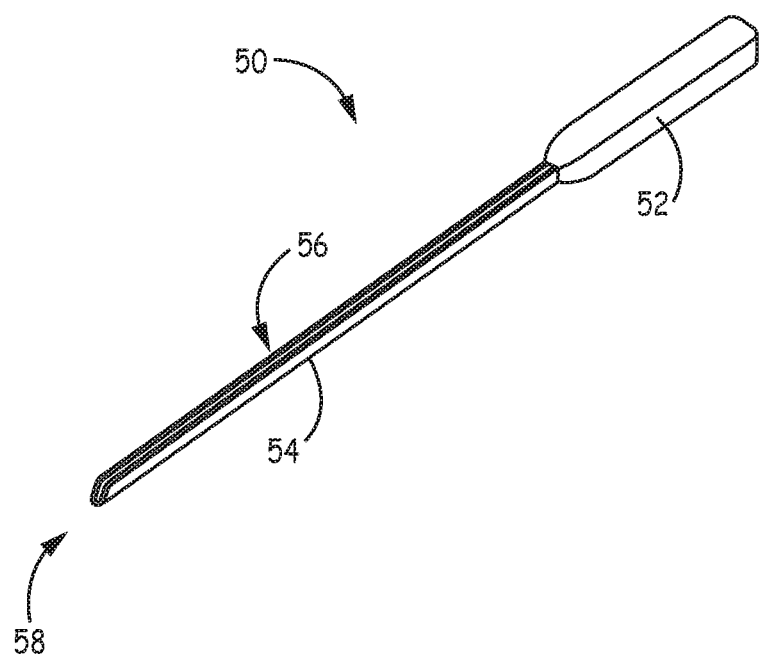
FIGS. 3A-F are conceptual drawings illustrating an example extravascular implant tool for implanting a medical lead, a catheter, or other implantable component.
Figure 3B:
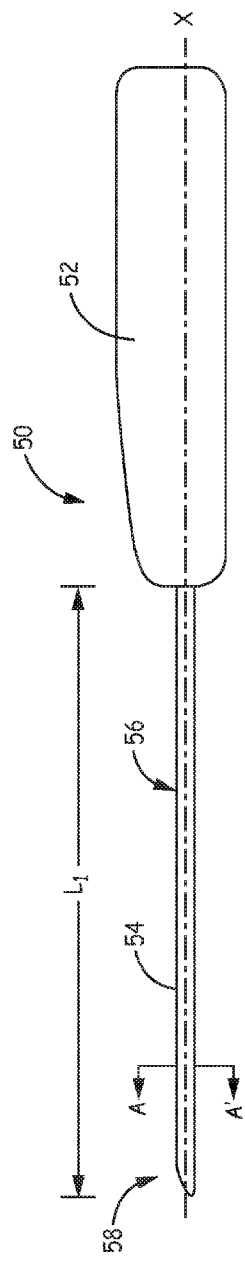
Figure 3C:
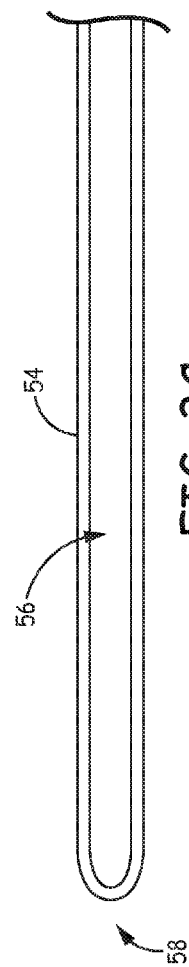
Figure 3D:
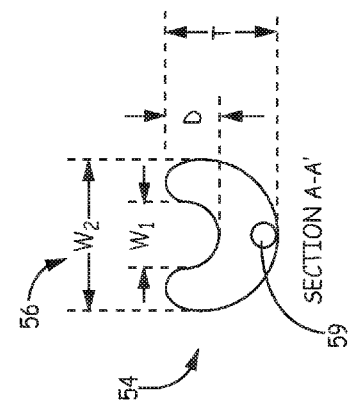
Figure 3E:
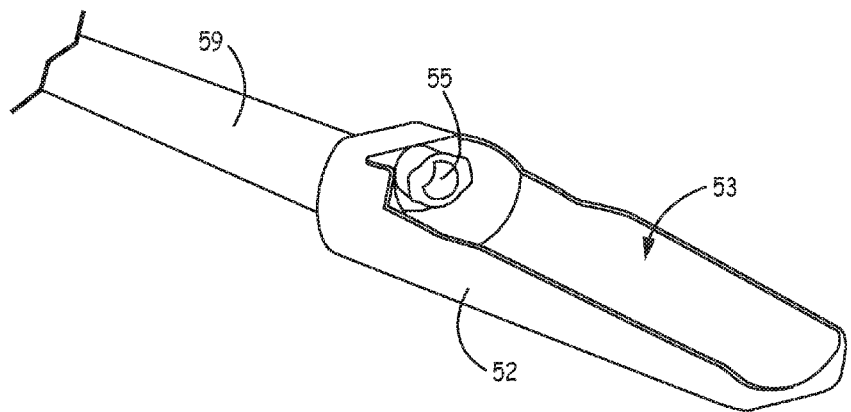
Figure 3F:
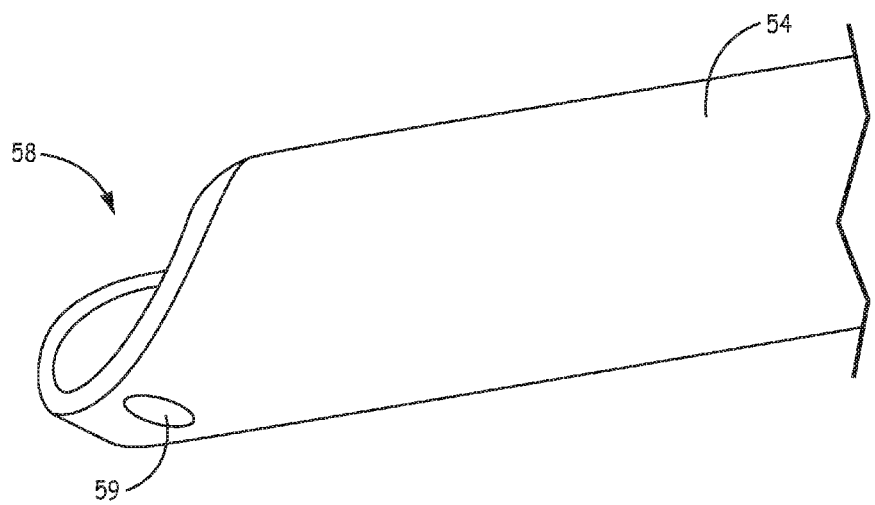

FIGS. 3A-F are conceptual drawings illustrating an example extravascular implant tool 30 for implanting a medical lead, such as lead 16 of FIGS. 1 and 2, a catheter, or other implantable component. FIG. 3A illustrates an angled view of implant tool 50. FIG. 3B illustrates a longitudinal side view of implant tool 50. FIG. 3C illustrates a top view of a shaft of implant tool 50. FIG. 3D illustrates a cross sectional view of a distal end of implant tool 50 taken from A-A' in FIG. 3B. FIG. 3E illustrates an example handle that includes a compartment or recess 53 to receive fluid delivery device. FIG. 3F illustrates an example distal end of shaft 54 having an opening of a lumen 59. As will be described in further detail herein, implant tool 50 of FIGS. 3A-F may be particularly useful in implanting defibrillation lead 16 in patient 12 in a subcutaneous, substernal, or other extravascular location.

Implant tool 50 includes a handle 52 and an elongate shaft 54 adjacent to handle 52. Shaft 54 defines an open channel 56 that extends from handle 52 to a distal end 58. Open channel 56 may extend the entire length of shaft 54 from handle 52 to distal end 58. Shaft 24 has a length, labeled "L1" in FIG. 3B. The length L1 of shaft 54 may be determined based on the desired tunneling application. For example, shaft 54 may have a length between approximately 5 to 11 inches in some instances. However, other lengths may be appropriate for other desired applications.

Shaft 54 may have a relatively uniform thickness along the longitudinal length of shaft 54, e.g., along major axis "X" defined by implant tool 50. Alternatively, the thickness of the walls of shaft 54 may not be uniform along the length of shaft 54. For example, the walls of shaft 54 may have an increased thickness toward distal end 58 compared to the proximal end of shaft 54. The increased thickness toward distal end 58 may enable improved tunneling performance by increasing rigidness or stiffness at distal end 58 or by reducing interference with the tissue. Additionally, the increased thickness of distal end 58 may aid in shaping distal end to avoid coring, cutting, or puncturing of tissue, pleura, pericardium or other parts of patient 12. In other instances, distal end 58 and the proximal end near handle 52 of shaft 54 may have a greater thickness compared to the middle portion of shaft 54.

As illustrated in the cross sectional view of distal end 58 of shaft 54 (FIG. 3D), taken perpendicular to the longitudinal length of shaft 54 from handle 52 to distal end 58 (e.g., orthogonal to the major axis X defined by implant tool 50), shaft 54 has a generally arc-shaped cross section that defines a generally arc-shaped open channel 56. In other examples, however, the cross-section of shaft 54 and open channel 56 may be formed into any of a number of different shapes including, but not limited to, a C-shape, U-shape, horseshoe-shape, or other shape.

Open channel 56 has a depth, labeled "D" in FIG. 3D. Depth D of channel 56 may, in one example, be approximately equal to an outer diameter the lead. In another example, the depth D of channel 56 may be less than the outer diameter of the lead. In further examples, the depth D of open channel 56 may be slightly larger than the outer diameter of the lead to provide some margin. In further instances, open channel 56 may be sized to account for the largest portion of the lead, such as a fixation mechanism (e.g., tines, mesh structure, or barbed-mesh structure), an anchoring sleeve, a connector, or other portion of the lead, with or without margin. The margin may allow the user push the lead along open channel 56 without too much interference or friction from surrounding tissue, muscle, or other bodily structures.

Open channel 56 also includes a width, labeled "W1" in FIG. 3D. In one example, width W1 of open channel 56 is greater than or equal to an outer diameter of the lead, catheter, or other component implant tool 50 is designed to implant. In another example, the body of shaft 54 may have a more C-like shape in which a gap or opening is formed to access open channel 56 and the gap or opening is less than the width W1 and is less than the outer diameter of the lead, catheter, or other component implant tool 50 is designed to implant. In this case, shaft 54 may include flexible portions (not illustrated in FIG. 3) that flex outward to allow the lead to be placed within the open channel 56 via the gap/opening. In other words, implant tool 50 may include flexible portions that form a gap or opening to access open channel 56. The flexible portions may be made from a flexible polymer to allow them to flex when placing a lead within open channel 56. The width of the gap or opening formed by the flexible portions is less than width W1. Flexible portions 57 function to keep the lead in place once inserted into open channel 56. In another example, width W of open channel 56 is approximately equal to the outer diameter of the lead such that when the implantable electrical lead 16 is placed within open channel 56 there is a slight interference fit. In further example, width W of open channel 56 is greater than an outer diameter of the lead (e.g., the diameter of the lead plus a slight margin).

Shaft 54 may have the same cross section along the entire length of shaft 54. Alternatively, shaft 54 may have varying cross sections along portions of the length of shaft 54. For example, may have a more open cross-section, e.g., a U-shaped cross-section toward a proximal end of shaft 54 and a C-shaped cross-section along the mid and distal sections of the shaft 54. Other varying cross-sections may be utilized without departing from the scope of this disclosure. Shaft 54 may have a total cross-sectional thickness (T) of between approximately 0.080-0.450 inches and a total width (W2) of approximately 0.080-0.450 inches.

In the examples described above, implant tool 50 may be to be used to implant a particular sized lead such that a different implant tool (e.g., having a different sized open channel 56) may be selected depending on the size of the lead to be implanted, which may range from 2 French to 11 French. In further examples, a single implant tool 50 may be designed to deliver leads having a variety of different diameters. In this case, the depth D and width W of open channel 56 may be sized for delivery of the largest diameter lead for which tool 50 is designed.

Shaft 54 may have a relatively uniform thickness along the sides and bottom of the body of shaft 54. In other words, the walls along the sides and bottom of shaft 54 may all have about the same thickness. In another example, however, shaft 54 may have thicker walls along the sides of shaft 54 forming open channel 56 than along the bottom of shaft 54.

Shaft 54 also includes a lumen 59 that extends from the proximal end connected to the handle 52 to a location near the distal end 58. Lumen 59 may be used to deliver fluid from a syringe or other fluid delivery device located near or within handle 52. In one example, handle 52 may include a coupler, such as a Luer fitting, that couples with a syringe or other fluid delivery device. The operator of tool 50 may inject fluid via lumen 59 for any of a number of purposes, including but not limited to pain reduction during and post tunneling, addition of fluids to minimize air around the lead electrodes during acute testing and/or for electrical noise reductions, for flushing out the subcutaneous and/or substernal tunnel formed by implant tool 30, and/or for the placement of antimicrobials agents to reduce infection potential. Lumen 59 may have any of a number of diameters depending upon the intended use of lumen 59.

Lumen 59 may be sized for use in other contexts in addition to or instead of delivery of fluid. For example, lumen 59 may be sized to receive a guide wire, a needle, or other structure that may be extended and retracted during tunneling of tool 50. In this manner, the operator may utilize the guide wire, needle or other structure to traverse the diaphragmatic attachments and/or any tissue, muscle, ligaments, or other structures in the tunneling path. In the case of a needle, for example, the user may extend the needle out the distal end of lumen 59 to pass through the diaphragmatic attachments and then retract the needle to continue tunnel with the blunt portion of shaft 54. In other examples, a radiopaque tube/rod can be placed in lumen 59 to provide radio-opacity to a polymer tunneling tool, an electrical probe can be positioned in lumen 59 to monitor electrical signals of the heart to provide impedance measurements of surrounding tissue, and/or lumen can be used to house a fiberscope for direct visualization.

In some instances, shaft 54 may include more than one lumen 59 extending down the length of shaft 54. For example, a first lumen may be used to provide fluids and the second lumen may be used for the guide wire, needle or other component. Although illustrated as being along a bottom of tool 50, lumen(s) 59 may be at other locations within the body of shaft 54, e.g., along one or both of the side walls. Lumen 59 is illustrated as having a circular cross-section, but lumen 59 may have different cross-sectional shapes. In one example, lumen 59 may be a shape similar to that of shaft 54 (e.g., C-shape, U-shape, or other arc shape). Lumen 59 may have an opening at the distal end of shaft 54 in one example (as illustrated in FIG. 3F). In another example, lumen 59 may have an opening that points away from the longitudinal length of shaft 54, e.g., outward from the outer diameter of one of the walls of shaft 54. In a further example, lumen 59 may open into open channel 56 near a distal end of channel 56.

Figure 8:
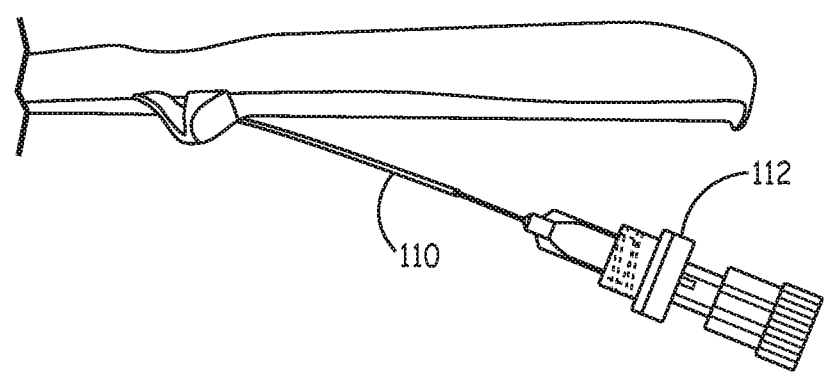
FIG. 8 illustrates an example handle that includes a tube and coupler that extend from the handle.

Handle 52 may, in some instances, include a compartment or recess 53 (illustrated in FIG. 3E). Handle 52 may include a removable portion that can be removed to expose compartment 53. Compartment 53 may, for example, be a recess sized to receive a fluid delivery device, such as a syringe, and hold the syringe in place during tunneling, e.g., by placing the removable portion of handle 52 over the syringe. In another example, compartment 53 may be a recess within which the syringe or other fluid delivery device is placed during tunneling without any separate piece of housing being placed over the recess. Handle 52 may also include a coupler 55 that connects to the syringe or other fluid delivery device to lumen 59. Thus, lumen 59 may extend into handle 52. In one example, the coupler 55 is a luer connector. The coupler 55 may be built into or on the body of the housing of handle 52 (as illustrated in FIG. 3E) or may include a tube 110 and coupler 112 that extends from the handle (e.g., as illustrated in FIG. 8).

Elongate shaft 54 of implant tool 50 is formed such that it is stiff enough to be capable of being pushed through the tissue, muscle or other structure to form a path through the body. Shaft 54 may be made of a metal, polymer, or other material or combination of materials, e.g., metal, metal alloy, polymer, or a combination thereof. Handle 52 of implant tool 50 may also be made of a metal, alloy, polymer, or other material or combination of materials. Handle 52 and elongate shaft 54 may, in some instances, be constructed of the same material. For example, implant tool 50 may be formed of a single, unitary piece of material, such as metal or rigid polymer. In other instances, handle 52 and elongate shaft 54 may be constructed of different materials. In this case, handle 52 and shaft 54 may be formed of separate components that are attached together to form implant tool 50, e.g., via a two piece construction. For example, handle 52 may be made of polymer and shaft 54 may be made of metal and attached to handle 52 to form implant tool 50. Example metals or metal alloys from which handle 52 or shaft 54 may be constructed include, but are not limited to, stainless steel, titanium, titanium alloys, nickel-cobalt, and nickel-cobalt alloys. Example polymers may include, but are not limited to, acetal resin (e.g., DELRIN®), polyether ether ketone (PEEK), polycarbonate, polypropylene composites, and liquid-crystal polymer (LCP). In addition, lubricious fillers and coatings may be used to improve lubricity during tunneling and lead insertion. Such additives or coatings include, but are not limited to, siloxane, PTFE, and Foster ProPell™. Example radiopaque additives may include, without limitation, BaSO4, WC, and Bi2O3.

Distal end 58 of shaft 54 may be shaped to aid in tunneling through tissue or muscle. For example, distal end 58 of the shaft 54 may be tapered, angled, blunt, rounded, pointed, bent or otherwise shaped to enable a user to tunnel through subcutaneous tissue without excess damage to surrounding tissue, piercing through the skin, or coring of the tissue.

A user of tool 50 may insert tool 50 into an incision and tunnel distal end 58 of shaft 54 to a desired location. Once at the desired location, the user may deliver an implantable electrical lead, such as defibrillation lead 16 of FIG. 1, catheter or other implantable structure in the tunnel or path formed by implant tool 50 by pushing the defibrillation lead 16 through open channel 56 of shaft 54 and then removing tool 50 while leave defibrillation lead 16 in the path created by the implant tool. As described above, lumen 59 may be used throughout the procedure for delivery of fluids and/or passing of other components (e.g., needles, guide wires, radiopaque elements, visualization components, or the like). In other instances, the implantable electrical lead 16 may be placed within open channel 56 prior to tunneling through the tissue or muscle such that the tunneling of the path and placement of lead 16 within the path occurs concurrently.

FIGS. 4A and 4B illustrate schematic diagrams of a implant tool 60. FIG. 4A illustrates a longitudinal side view of implant tool 60. FIG. 4B illustrates a cross sectional view of implant tool 50 taken from B-B' in FIG. 4A. Implant tool 60 includes a handle 62, a shaft 64, an open channel 66, and a distal end 68. Handle 62, shaft 64, open channel 66, and distal end 68 of implant tool 60 may conform substantially to handle 32, shaft 34, open channel 36 and distal end 38 of implant tool 30 described above with respect to FIGS. 3A-F (e.g., include one or more of the structures, dimensions, materials, properties, functions, or features described with respect to FIGS. 3A-F), except shaft 64 does not include a built-in lumen 59. Instead, shaft 64 includes another open channel 69 that extends from the proximal end of shaft 64 near handle 62 to a distal end 68 of shaft 64 (illustrated in FIG. 4B). Open channel 69 is sized and configured to receive a tube and hold the tube in place during tunneling and removal of shaft 64. In one example, handle 62 may include a lumen that extends from open channel 69 to a coupler 55 within, on, or coupled to handle 62. In this example, the tube may extend through the lumen of handle 62 and into open channel 69.

Figure 5A:
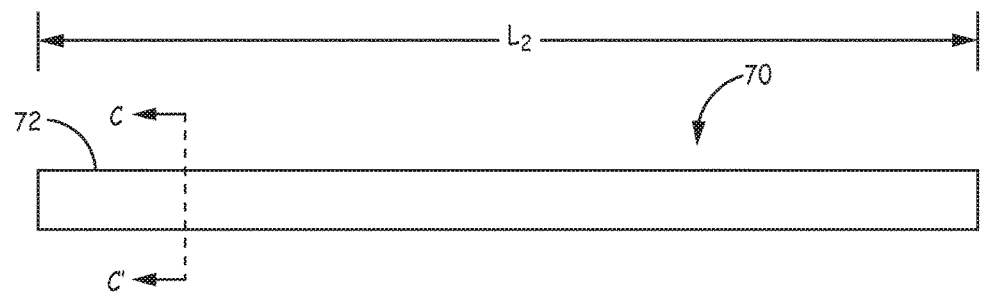
FIGS. 5A-5D illustrate an example sheath that may be used in conjunction with the extravascular implant tool of FIGS. 4A and 4B.
Figure 5B:
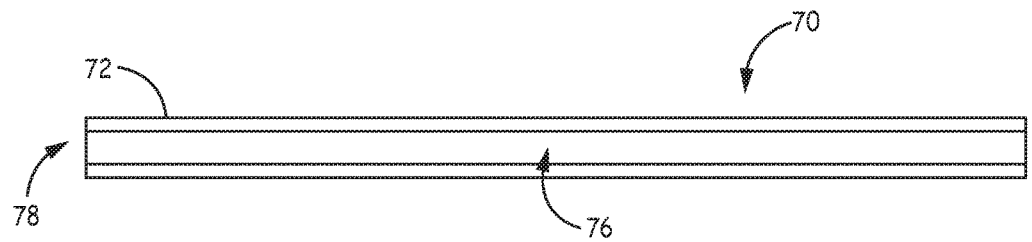
Figure 5C:
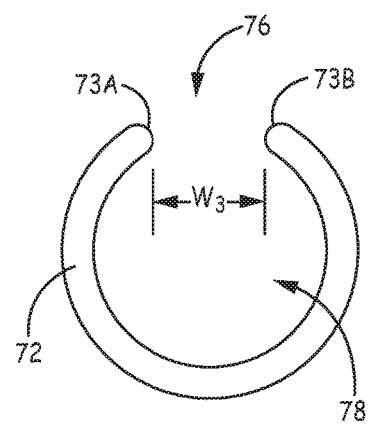
Figure 5D:
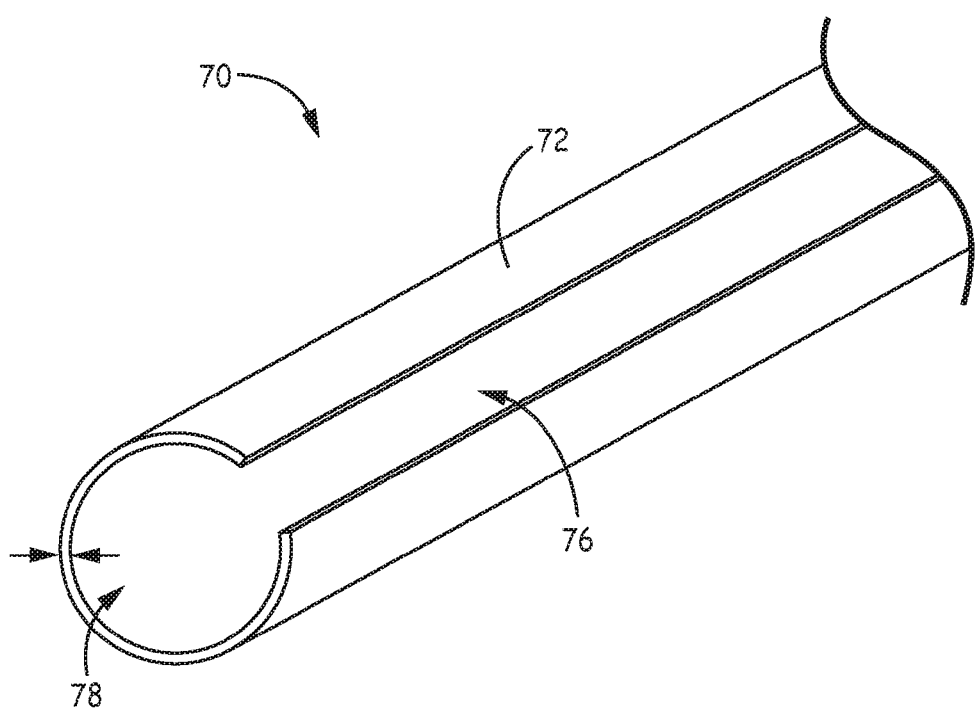

FIGS. 5A-5D illustrate an example sheath 70 that may be used in conjunction with implant tool 60 of FIGS. 4A and 4B to form a delivery system. FIG. 5A illustrates a longitudinal side view of sheath 70. FIG. 5B illustrates a top view of example sheath 70. FIG. 5C illustrates a cross sectional view of example sheath 70 taken from C-C' in FIG. 5A. FIG. 5D illustrates an angled view of example sheath 70. Sheath 70 is configured to be placed over shaft 64 of implant tool 60. Sheath 70 may thereby reduce the likelihood of the tube exiting open channel 69. Alternatively, sheath 70 and shaft 64 may form a lumen via the friction fit between the body of the sheath 70 and the shaft 64, described in more detail below. In this alternative example, there is no need for a separate tube placed within open channel 69.

Sheath 70 has a length (L2) that is less than the length (L1) of shaft 64 of implant tool 60. As such, when sheath 70 is placed over shaft 64 of implant tool 60, shaft 64 extends from the distal end of sheath 70. As illustrated best in FIG. 5C, the arc length of sheath 70 may, in some examples, be greater than the arc length of shaft 64 such that the ends of the opening of sheath 70 extend over open channel 66 to aid in holding a lead or other component within open channel 66. Sheath 70 may also be moveable with respect to shaft 64. For example, sheath 70 may be rotated around the major axis "X" of deliver tool 60 such that opening 76 of sheath 70 may rotate around the body of shaft 64 of implant tool 60.

Sheath 70 includes a body 72 having a proximal end and a distal end. In some instances, the distal end of body 72 may be tapered to aid in tunneling. Body 72 of sheath 70 defines an inner channel 78. In the examples described herein, the cross-section of an outside of body 72 and the inner channel 78 defined by body 72 is substantially C-shaped. However, the cross-section of either the outside of body 72 and/or the inner channel 78 defined by body 72 may be a different shape depending on the desired application. The cross-section is taken normal (i.e., perpendicular) to the longitudinal length of sheath 70 from the distal end of body 72 to the proximal end of body 72.

Sheath 70 includes an opening 76 along the length of body 72. As described further herein, opening 76 along body 72 may form a gap between the ends of body 72 located at the boundary of the opening (as can be viewed in the cross-sectional view of sheath 70). Inner channel 78 is accessible via opening 76. Opening 76 extends the entire length of body 72 from the distal end to the proximal end. In other examples, opening 76 may not extend the entire length of the body 72. Inner channel 78 is accessible via opening 76. In the example illustrated in FIGS. 6, opening 76 follows a substantially straight path from the distal end of body 72 of sheath 70 to the proximal end of body 72 of sheath 70. In alternative configurations, however, opening 76 may follow other paths from the distal end of body 72 to the proximal end of body 72, such as spiral path, serpentine path, meandering path, or other path.

Sheath 70 may be sized such that sheath 70 fits on shaft 64 of implant tool 60 in such a manner that an interference fit is achieved between sheath 70 and shaft 64. The interference fit is achieved by friction after the parts are pushed together, rather than by any other means of fastening. The interference fit may, in some instances, be achieved by sizing and/or shaping the two mating parts so that one or the other, or both, slightly deviate in size from the nominal dimension. The interference fit may therefore be viewed as referring to the fact that one part slightly interferes with the space that the other is taking up. The tightness of the interference fit may be controlled by the amount of allowance, e.g., the planned difference from nominal size. Different allowances will result in various strengths of fit. The value of the allowance depends on which material is being used, how big the parts are, and what degree of tightness is desired.

In one example, the diameter of the inner channel 78 formed by body 72 of sheath 70 may be equal to or slightly smaller than the outer diameter of shaft 64. The allowance in this case may be on the order of 1-10 thousandths of an inch. Allowances of less than 1 thousandth and greater than 10 thousands may be used, however. As such, when placed over shaft 64, sheath 70 slightly expands in diameter causing the interference fit. Other techniques for achieving an interference fit may also be utilized.

FIG. 5C illustrates a cross-sectional view of the distal end of sheath 70 taken from C-C'. As illustrated in FIG. 5C, body 72 is C-shaped such that opening 76 defines a gap between end 73A and end 73B of body 72. In other words, a gap exists along the circumference or cross-section of body 72. Opening 76 may have a width "W3." Width W3 may, in some instances, be less than width W1 of channel 66 of shaft 64. Body 72 defines a channel 78 that extends along the length of body 72 from the distal end to the proximal end. In this case, channel 78 is a C-shaped channel, but the shape of channel 78 may vary depending on the cross-sectional shape of body 72. In some instances, opening 76 may have the same width W3 along the entire length of the body 72. In other instances, the width of opening 76 at the proximal end of sheath 70 has is larger than width W3 at the distal end of body 72.

Sheath 70 may be formed to have a thickness 79 that may vary depending the type of material used to form sheath 70, the desired rigidity of sheath 70, or the like. Sheath 70 should be rigid enough to not crumple, wrinkle, crease, or crush while being tunneled through tissue of patient 12. Sheath 70 may be made of extruded or molded material. The material may include, but not limited to, a polymer, a copolymer, a thermoplastic, or other material. Example materials include, but are not limited to, polyether block amide (such as PEBAX® 72D), polyether block amide blends (PEBAX® with a Foster ProPell™ additive), polyethylene, ultra-high-molecular-weight polyethylene (UHMWPE), Polytetrafluoroethylene (PTFE), nylons (such as GRILAMID® TR55 or L25, VESTAMID® L2140, AESNO®), or the like. In some instances, sheath 70 may be made of multiple layers of different materials or may vary in materiality and durometer along the length of body 72. For example, sheath 70 may be formed of PEBAX® with a PTFE lining the inner surface of the channel. Other additives or coatings that may be applied to increase lubricity include, but are not limited to, siloxane, PTFE, and Foster ProPell™

Opening 76 may vary in size depending upon the desired application. Opening 76 may be less than the diameter of lead 16. In one example, opening 76 may be approximately 10% less than the diameter of lead 16. However, in other examples, opening 76 may be less than 10% of the diameter of lead 16 or more than 10% of the diameter of lead 16. Opening 76 may be larger or smaller than illustrated in FIGS. 5A-D.

Figure 6:
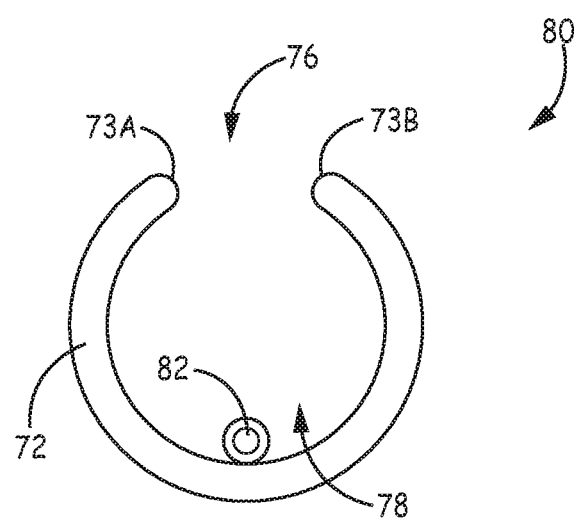
FIG. 6 illustrates as cross sectional view of a body of another example sheath.

FIG. 6 illustrates as cross sectional view of another example sheath 80. Sheath 80 may conform substantially to sheath 70 of FIGS. 5A-D, e.g., include one or more of the structures, dimensions, materials, properties, functions, or features described with respect to FIGS. 5A-D, except sheath 80 incorporates the tubing that fits within open channel 69 such that the tubing is an integral part of sheath 80. In other words, body 72 of sheath 80 is formed to include a lumen 82. Lumen 82 extends inward from an interior surface of sheath body 84. Lumen 82 is sized to fit within channel 69 of shaft 64 of implant tool 60.

Figure 7:
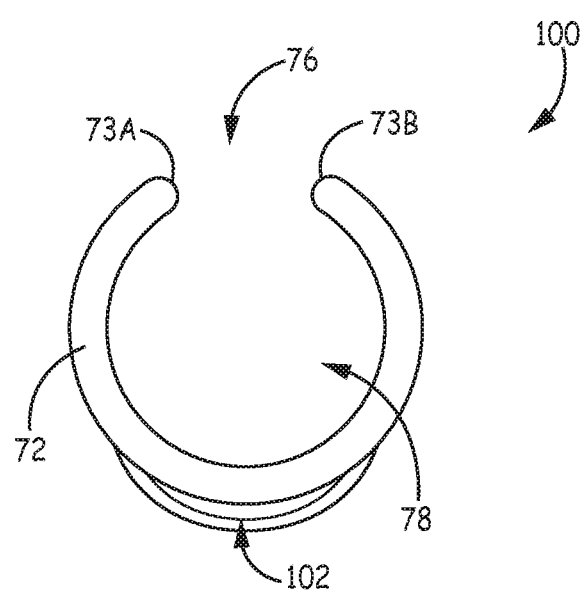
FIG. 7 illustrates another example delivery system that includes a implant tool and a sheath having a lumen.

FIG. 7 illustrates another example delivery system that includes a implant tool 90 and a sheath 100. Implant tool 90 conforms substantially to implant tool 50 described above with respect to FIGS. 3A-F or implant tool 70 of FIGS. 4A and 4B, except that implant tool 90 does not include a lumen or a second open channel. Sheath 100 may conform substantially to sheath 70 of FIGS. 5A-D and sheath 90 of FIG. 6, except the lumen 102 of sheath 100 extends outward from an outer surface of sheath body 72. Fluids may be delivered during the procedure using the lumen of sheath 100.

The implant tools and/or systems described herein may be used to implant medical leads, catheters, or other implantable component. In one example, the implant tools and/or systems described herein may be used to implant a medical electrical lead at least partially within the substernal space, e.g., within anterior mediastinum of patient 12. Alternatively or additionally, the implant tools and/or systems described herein may be used to implant a medical electrical lead along subcutaneous paths above the ribcage/sternum.

In one example, implant tool 50 (or other tool described herein) is introduced into an incision near the center of the torso of patient 12. Implant tool 50 is advanced from the incision superior along the sternum either substernally or subcutaneously. The distal end of lead 16 (or other lead, catheter or implantable component) is introduced into open channel 56 of shaft 54 near the incision. The distal end of lead 16 is advanced along open channel 56 from the incision toward distal end 58 of shaft 54. Implant tool 50 is withdrawn toward the incision and removed from the body of patient 12 while leaving defibrillation lead 16 in place along the path along the sternum.

Implant tool 50 may be used to form a subcutaneous tunnel lateral between the center of the torso of the patient to a pocket on the left side of the patient. Lead 16 may be advance along channel 56 and implant tool 50 may be removed leaving the proximal portion of lead 16 in place along the lateral path. This may be done before or after implanting the distal portion of lead 16.

During the implantation, the operator of tool 50 (or other tool described herein) may inject fluid via lumen 59 for any of a number of purposes, including but not limited to pain reduction during and post tunneling, addition of fluids to minimize air around the lead electrodes during acute testing and/or for electrical noise reductions, for flushing out the subcutaneous and/or substernal tunnel formed by implant tool 30, and/or for the placement of antimicrobials agents to reduce infection potential.

Various examples have been described. However, the exampled described herein should not be limiting of the contents of this disclosure. In other examples, the open channel tool may not include a lumen or a second open channel for receiving a tube. Instead, a sheath may be used in conjunction with the open channel tool and the sheath may include a lumen built into the sheath. In another example, a tubular fluid lumen is placed directly into the main channel during tunneling. To aid it staying in position during tunneling the tubing incorporates clip/marker feature to assure tubing remains in place during tunneling. The lumen can also be formed with a shape similar to shaft to help hold the sheath in place before and during tunneling. With this embodiment, fluid can be administered during tunneling and prior to lead introductions.

These and other examples are within the scope of the following claims.

The invention claimed is:

1. An implant tool comprising:
a handle; and
a shaft adjacent the handle, the shaft including a shaft body having a proximal end adjacent the handle and a distal end, and an exterior surface extending from the proximal end to the distal end,
wherein the exterior surface of the shaft body defines an open channel that extends on an exterior of the shaft body from near the proximal end to the distal end, wherein the exterior surface of the shaft body defines a concave portion of the open channel,
wherein the shaft body defines at least one lumen positioned within the shaft body that extends from the proximal end of the shaft body to a location near the distal end of the shaft body, and
wherein the at least one lumen includes an opening that opens into the open channel of the shaft body near the distal end of the shaft body.

2. The implant tool of claim 1, wherein the at least one lumen comprises two or more lumens.

3. The implant tool of claim 1, further comprising a coupler configured to connect to a fluid delivery device such that the at least one lumen is in fluid communication with the fluid delivery device.

4. The implant tool of claim 3, further comprising a syringe that connects to the coupler.

5. The implant tool of claim 3, wherein the handle includes one of a compartment and a recess configured to receive the fluid delivery device.

6. An implant tool comprising:
a handle;
a shaft adjacent the handle, the shaft including a shaft body having a proximal end adjacent the handle and a distal end, and an exterior surface extending from the proximal end to the distal end,
wherein the exterior surface of the shaft body defines a first open channel that extends on an exterior of the shaft body from near the proximal end to the distal end, wherein the exterior surface of the shaft body defines a concave portion of the first open channel,
wherein the exterior surface of the shaft body defines a second open channel that extends on an exterior of the shaft body from near the proximal end to a location near the distal end, wherein the exterior surface of the shaft body defines a concave portion of the second open channel, and
wherein the first open channel is larger than the second open channel; and
a fluid delivery tube within the second open channel.

7. The implant tool of claim 6, wherein the first open channel has a width that is greater than or equal to an outer diameter of an implantable medical lead.

8. The implant tool of claim 6, further comprising a sheath configured to be placed on the shaft of the implant tool, the sheath including:
a sheath body having a proximal end and a distal end,
a sheath channel formed by the sheath body, the sheath channel extending from the proximal end to the distal end of the sheath body, and
an opening that extends along the sheath body from the proximal end to the distal end,
wherein, when the sheath is placed over the shaft of the implant tool, the first open channel of the shaft is accessible via the opening of the sheath and the sheath body holds the fluid delivery tube within the second open channel.

9. The implant tool of claim 6, further comprising a sheath configured to be placed on the shaft of the implant tool, the sheath including:
a sheath body having a proximal end and a distal end,
a sheath channel formed by the sheath body, the sheath channel extending from the proximal end to the distal end of the sheath body, and
an opening that extends along the sheath body from the proximal end to the distal end,
wherein the fluid delivery tube is integrated into the sheath body, and wherein the fluid delivery tube is configured to be placed within the second open channel of the shaft of the implant tool when the sheath is placed over the shaft.

10. The implant tool of claim 6, further comprising a coupler configured to connect to a fluid delivery device such that the fluid delivery tube is in fluid communication with the fluid delivery device.

11. The implant tool of claim 10, further comprising a syringe that connects to the coupler.

12. The implant tool of claim 10, wherein the handle includes one of a compartment and a recess configured to receive the fluid delivery device.

* * * * *